United States Patent
Arar et al.

(10) Patent No.: US 11,432,746 B2
(45) Date of Patent: Sep. 6, 2022

(54) METHOD AND SYSTEM FOR DETECTING HEARING IMPAIRMENT

(71) Applicant: International Business Machines Corporation, Armonk, NY (US)

(72) Inventors: Raphael I. Arar, San Jose, CA (US); Chris Kau, Mountain View, CA (US); Jonathan D. Dunne, Dungarvan (IE)

(73) Assignee: International Business Machines Corporation, Armonk, NY (US)

( * ) Notice: Subject to any disclaimer, the term of this patent is extended or adjusted under 35 U.S.C. 154(b) by 594 days.

(21) Appl. No.: 16/511,894

(22) Filed: Jul. 15, 2019

(65) Prior Publication Data
US 2021/0015404 A1   Jan. 21, 2021

(51) Int. Cl.
*A61B 5/12* (2006.01)
*H04R 25/00* (2006.01)

(52) U.S. Cl.
CPC .......... *A61B 5/121* (2013.01); *H04R 25/554* (2013.01); *H04R 25/30* (2013.01); *H04R 2225/41* (2013.01)

(58) Field of Classification Search
CPC ......... A61B 5/121; A61B 5/123; A61B 5/746; H04R 2225/41; H04R 25/30; H04R 25/554; H04R 27/02
See application file for complete search history.

(56) References Cited

U.S. PATENT DOCUMENTS

| | | | |
|---|---|---|---|
| 4,777,474 A | 10/1988 | Clayton | |
| 6,602,202 B2 | 8/2003 | John et al. | |
| 9,754,465 B2 * | 9/2017 | Gordon | G08B 7/06 |
| 2004/0064066 A1 | 4/2004 | John et al. | |
| 2005/0135644 A1 * | 6/2005 | Qi | H04R 25/505 381/314 |
| 2007/0195781 A1 * | 8/2007 | Yuki | H04L 29/12113 370/392 |
| 2008/0194984 A1 | 8/2008 | Keefe | |
| 2011/0025499 A1 | 2/2011 | Hoy et al. | |
| 2013/0034234 A1 | 2/2013 | Chen et al. | |

(Continued)

FOREIGN PATENT DOCUMENTS

WO    WO-2017121882 A1 *  7/2017  .............. H04W 4/80

OTHER PUBLICATIONS

Stecanella, B. (Jun. 22, 2017). Support Vector Machines (SVM) algorithm explained. MonkeyLearn Blog. Retrieved May 3, 2022, from https://monkeylearn.com/blog/introduction-to-support-vector-machines-svm/ (Year: 2017).*

*Primary Examiner* — Thaddeus B Cox
*Assistant Examiner* — Marc D. Honrath
(74) *Attorney, Agent, or Firm* — Sherman IP LLP; Kenneth L. Sherman; Hemavathy Perumal

(57) ABSTRACT

One embodiment of the present invention provides a method comprising running a monitoring agent on a connected electronic device, and determining, via the monitoring agent, a level of hearing impairment of an individual user associated with the connected electronic device. The method further comprises, in response to determining the individual user has some level of hearing impairment, selecting a notification mechanism suitable for notifying the individual user based on the level of hearing impairment, and invoking the monitoring agent to notify the individual user of an event in accordance with the notification mechanism selected.

20 Claims, 5 Drawing Sheets

(56) References Cited

U.S. PATENT DOCUMENTS

| | | | |
|---|---|---|---|
| 2013/0100268 A1 | 4/2013 | Mihailidis et al. | |
| 2013/0142350 A1* | 6/2013 | Larsen | H04R 1/1041 |
| | | | 381/74 |
| 2014/0309549 A1* | 10/2014 | Selig | A61B 5/123 |
| | | | 600/559 |
| 2016/0125726 A1 | 5/2016 | Gordon et al. | |
| 2016/0135719 A1* | 5/2016 | von Kraus | A61B 90/36 |
| | | | 600/559 |
| 2016/0292997 A1 | 10/2016 | Milne | |
| 2016/0337743 A1 | 11/2016 | Neeley | |
| 2016/0381450 A1 | 12/2016 | Taite et al. | |
| 2019/0045293 A1* | 2/2019 | Blau | A61B 5/0004 |

* cited by examiner ately pointed out in the claims
METHOD AND SYSTEM FOR DETECTING HEARING IMPAIRMENT The present invention generally relates to the field of hearing impairment detection and assistance, and more specifically, to a method and system for detecting hearing impairment and notifying an individual with hearing impairment of an event.

SUMMARY

One embodiment of the present invention provides a method comprising running a monitoring agent on a connected electronic device, and determining, via the monitoring agent, a level of hearing impairment of an individual user associated with the connected electronic device. The method further comprises, in response to determining the individual user has some level of hearing impairment, selecting a notification mechanism suitable for notifying the individual user based on the level of hearing impairment, and invoking the monitoring agent to notify the individual user of an event in accordance with the notification mechanism selected.

Another embodiment of the present invention provides a system comprising at least one processor, and a non-transitory processor-readable memory device storing instructions that when executed by the at least one processor causes the at least one processor to perform operations. The operations include running a monitoring agent on a connected electronic device, and determining, via the monitoring agent, a level of hearing impairment of an individual user associated with the connected electronic device. The operations further include, in response to determining the individual user has some level of hearing impairment, selecting a notification mechanism suitable for notifying the individual user based on the level of hearing impairment, and invoking the monitoring agent to notify the individual user of an event in accordance with the notification mechanism selected.

One embodiment of the present invention provides a computer program product comprising a computer readable storage medium having program instructions embodied therewith. The program instructions are executable by a processor to cause the processor to run a monitoring agent on a connected electronic device, and determine, via the monitoring agent, a level of hearing impairment of an individual user associated with the connected electronic device. The program instructions are further executable by the processor to cause the processor to, in response to determining the individual user has some level of hearing impairment, select a notification mechanism suitable for notifying the individual user based on the level of hearing impairment, and invoke the monitoring agent to notify the individual user of an event in accordance with the notification mechanism selected.

These and other aspects, features and advantages of the invention will be understood with reference to the drawing figures, and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

Figure 1:
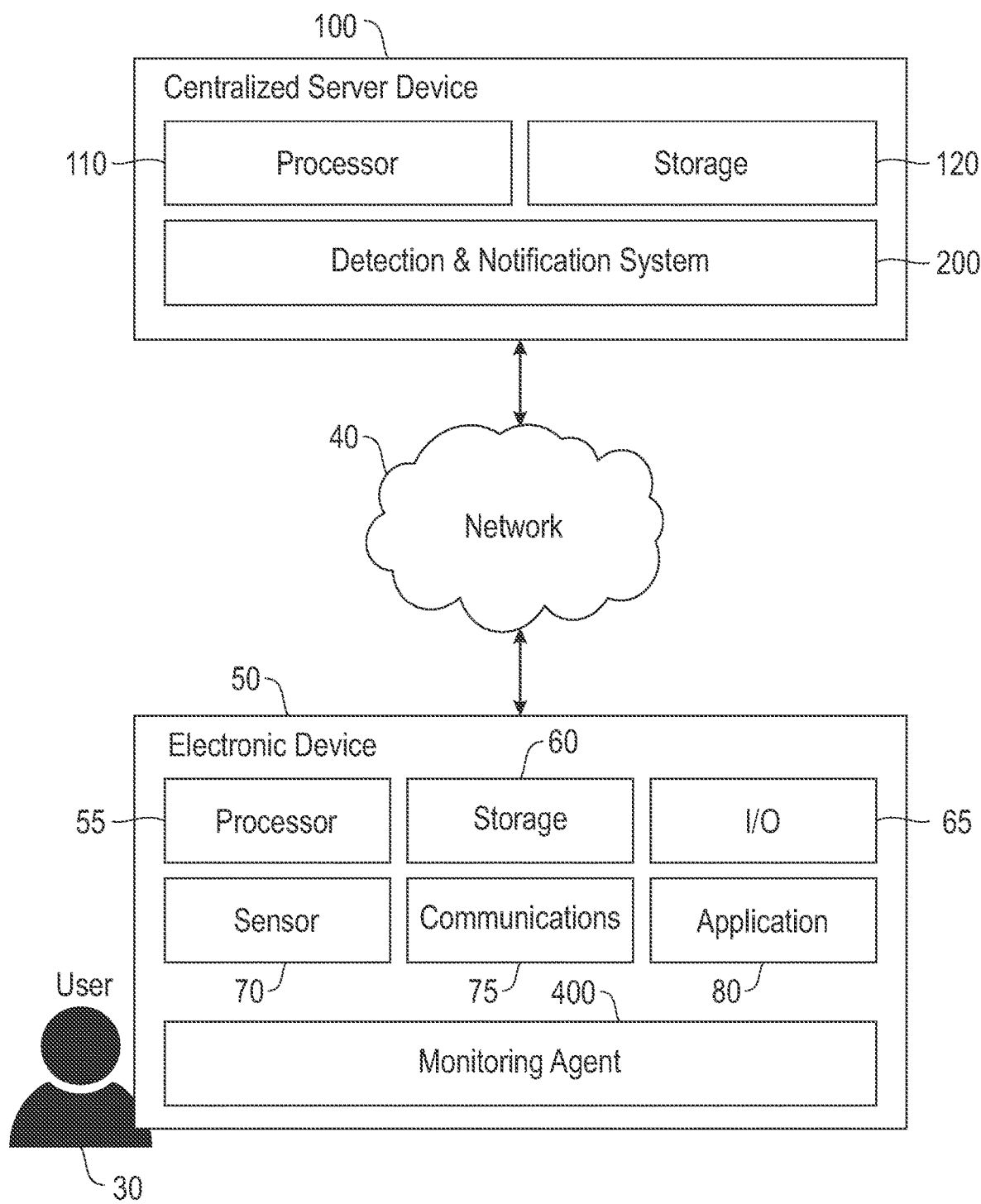
FIG. 1 illustrates an example computing framework for detecting hearing impairment, in accordance with an embodiment of the invention.

The detailed description explains the preferred embodiments of the invention, together with advantages and features, by way of example with reference to the drawings.

DETAILED DESCRIPTION

The present invention generally relates to the field of hearing impairment detection and assistance, and more specifically, to a method and system for detecting hearing impairment and notifying an individual with hearing impairment of an event. One embodiment of the present invention provides a method comprising running a monitoring agent on a connected electronic device, and determining, via the monitoring agent, a level of hearing impairment of an individual user associated with the connected electronic device. The method further comprises, in response to determining the individual user has some level of hearing impairment, selecting a notification mechanism suitable for notifying the individual user based on the level of hearing impairment, and invoking the monitoring agent to notify the individual user of an event in accordance with the notification mechanism selected.

Another embodiment of the present invention provides a system comprising at least one processor, and a non-transitory processor-readable memory device storing instructions that when executed by the at least one processor causes the at least one processor to perform operations. The operations include running a monitoring agent on a connected electronic device, and determining, via the monitoring agent, a level of hearing impairment of an individual user associated with the connected electronic device. The operations further include, in response to determining the individual user has some level of hearing impairment, selecting a notification mechanism suitable for notifying the individual user based on the level of hearing impairment, and invoking the monitoring agent to notify the individual user of an event in accordance with the notification mechanism selected.

One embodiment of the present invention provides a computer program product comprising a computer readable storage medium having program instructions embodied therewith. The program instructions are executable by a processor to cause the processor to run a monitoring agent on a connected electronic device, and determine, via the monitoring agent, a level of hearing impairment of an individual user associated with the connected electronic device. The program instructions are further executable by the processor to cause the processor to, in response to determining the individual user has some level of hearing impairment, select a notification mechanism suitable for notifying the individual user based on the level of hearing impairment, and invoke the monitoring agent to notify the individual user of an event in accordance with the notification mechanism selected.

For expository purposes, the terms "hearing impairment" and "hearing loss" are used interchangeably herein. Hearing loss can result from a variety of issues such as, but not limited to, aging, noise exposure (e.g., long-term exposure to loud noise, short-term exposure to very loud noise), disease, infection, traumatic injury, and heredity. Some individuals have permanent hearing impairment. Some individuals may have temporary hearing impairment due to external circumstances or factors. For example, in a workplace, some employees wearing headphones or operating loud machinery may not hear particular audible events, such as audio announcements or alerts of an emergency made via a public address (PA) or other speaker system.

Conventional solutions provide methods and systems for detecting biological hearing impairment and/or assessing or evaluating biological auditory functions of an individual. None of these conventional solutions, however, provide methods and systems for detecting temporary hearing impairment of an individual due to external circumstances or factors.

Embodiments of the invention provide a method and system for detecting temporary hearing impairment of an individual due to external circumstances or factors. One embodiment provides a method and system for determining an individual's level (i.e., degree) of hearing impairment, and selecting a notification mechanism best suited for alerting or notifying the individual of an event (e.g., an emergency) based on the individual's level of hearing impairment.

FIG. 1 illustrates an example computing framework 10 for detecting hearing impairment and notifying an individual with hearing impairment of an event, in accordance with an embodiment of the invention. The framework 10 comprises a centralized server device 100. The centralized server device 100 comprises computation resources such as, but not limited to, one or more processor units 110 and one or more storage units 120. One or more applications may execute or operate on the centralized server device 100 utilizing the computation resources of the centralized server device 100.

In one embodiment, the applications on the centralized server device 100 include, but are not limited to, a detection and notification system 200 configured to detect one or more individual users 30 with hearing impairment (e.g., permanent hearing impairment, temporary hearing impairment due to external circumstances or factors) based on one or more electronic devices 50 associated with the one or more individual users 30. An electronic device 50 is associated with an individual user 30 if the electronic device 50 is operated or utilized by the individual user 30, or is within proximity of the individual user 30.

In one embodiment, the detection and notification system 200 is configured to, for each individual user 30 detected with hearing impairment, determine one or more notification mechanisms suitable for alerting or notifying the individual user 30, and invoking the one or more notification mechanisms determined on at least one electronic device 50 associated with the individual user 30 to alert or notify the individual user 30 of an event. Examples of different notification mechanisms include, but are not limited to, a haptic notification mechanism (e.g., producing a haptic alert, such as a vibration, via a haptic sensor of a haptic-enabled electronic device 50), an audio notification mechanism (e.g., producing an audio alert, such as a beep or an audio message, via a speaker of an electronic device 50), a visual notification mechanism (e.g., producing a visual alert, such as a solid or flashing light in red or another active color, via a light indicator of an electronic device 50; displaying an overlay of an alert message on a display screen of an electronic device 50), a lock notification mechanism (e.g., locking a component, such as a display screen, a keyboard, and/or a touch interface, of a connected electronic device 50), etc.

In one embodiment, the detection and notification system 200 is configured to exchange data with one or more electronic devices 50 connected to a same communication network 40 as the centralized server device 100 over a connection (e.g., a wireless connection such as a Wi-Fi connection or a cellular data connection, a wired connection, or a combination of the two).

In one embodiment, an electronic device 50 comprises one or more computation resources such as, but not limited to, one or more processor units 55 and one or more storage units 60. One or more applications 80 may execute or operate on an electronic device 50 utilizing the one or more computation resources of the electronic device 50.

Examples of an electronic device 50 include, but are not limited to, a desktop computer, a mobile electronic device (e.g., a tablet, a smart phone, a laptop, etc.), a wearable device (e.g., a smart watch, etc.), an Internet of Things (IoT) device, a smart appliance such as a smart television, etc.

In one embodiment, an electronic device 50 comprises a communications unit 75 configured to exchange data with one or more other devices (e.g., the centralized server device 100, another electronic device 50, a secondary device, etc.) connected to a same communication network 40 as the electronic device 50. The communications unit 75 may comprise any suitable communications circuitry operative to connect to the communication network 40 and to exchange data from the electronic device 50 with the one or more other devices connected to the same communication network 40. The communications unit 75 may be operative to interface with the communication network 40 using any suitable communications protocol such as, for example, Wi-Fi (e.g., an IEEE 752.11 protocol), Bluetooth®, high frequency systems (e.g., 900 MHz, 2.4 GHz, and 5.6 GHz communication systems), infrared, GSM, GSM plus EDGE, CDMA, quadband, and other cellular protocols, VOIP, TCP-IP, or any other suitable protocol.

In one embodiment, an electronic device 50 comprises one or more input/output (I/O) units 65 integrated in or coupled to the electronic device 50, such as a keyboard, a keypad, a touch interface, a display screen, a speaker, a light indicator, etc. A user 30 may utilize an I/O unit 65 of an electronic device 50 to configure one or more user preferences (e.g., preferred notification mechanism), configure one or more parameters, provide input (e.g., a user response to an alert or notification, a test pulse), etc.

In one embodiment, an electronic device 50 comprises one or more sensor units 70 integrated in or coupled to the electronic device 50, such as a camera, a microphone, a GPS, a motion sensor, a haptic sensor, etc. A sensor unit 70 may be utilized to capture content and/or sensor-based contextual information. For example, an application 80 on the electronic device 50 may utilize at least one sensor unit 70 to capture content and/or sensor-based contextual information, such as a microphone for audio data (e.g., voice commands, ambient noise, etc.), a camera for image data (e.g., still and/or video images of a user 30 and/or an environment surrounding the electronic device 50, etc.), a GPS for location data (e.g., location coordinates), a motion sensor for proximity or motion data (e.g., data indicative of whether a user 30 is within proximity of the electronic device 50, etc.

In one embodiment, one or more applications 75 on an electronic device 50 include a monitoring agent 400. The monitoring agent 400 is a companion application for the system 200 that is configured to exchange data with the system 200. As described in detail later herein, in one embodiment, the monitoring agent 400 is configured to: (1) continuously monitor whether a secondary device is connected to the electronic device 50 (e.g., wireless headphones connected to the electronic device 50 via Bluetooth®, wired headphones plugged into an I/O unit 65 of the electronic device 50, such as a headphone jack or an audio output connector, etc.), and (2) in response to detecting a secondary device is connected to the electronic device 50, send a data message to the system 200, wherein the data message indicates that the secondary device is connected to the electronic device 50.

In one embodiment, one or more applications 80 on an electronic device 50 may further include one or more software mobile applications loaded onto or downloaded to the electronic device 50, such as a camera application, a social media application, etc.

Figure 2:
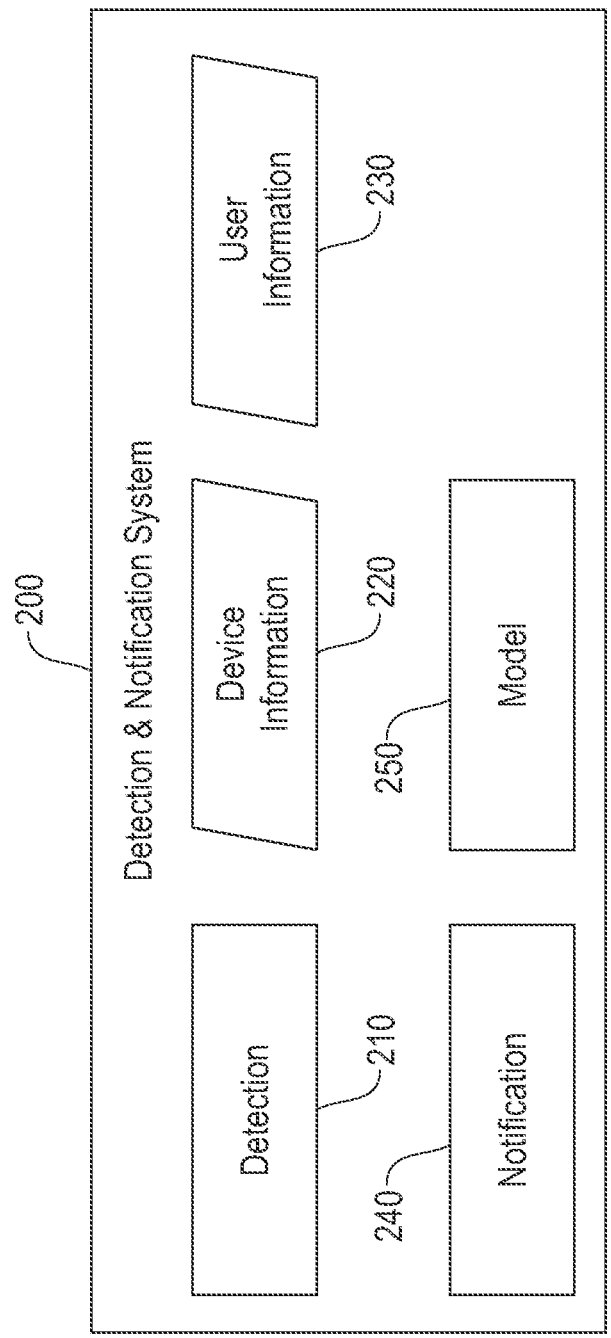
FIG. 2 illustrates an example detection and notification system, in accordance with an embodiment of the invention.

FIG. 2 illustrates an example detection and notification system 200, in accordance with an embodiment of the invention. In one embodiment, the system 200 comprises a detection unit 210 configured to generate device information 220 comprising a list of all electronic devices 50 connected to a same network (e.g., communication network 40 in FIG. 1) as the system 200. For expository purposes, the term "connected electronic device" as used herein generally refers to an electronic device 50 connected to a same network as the system 200. In one embodiment, the detection unit 210 compiles the list of connected electronic devices 50 based on a broadcast of each IP address of each connected electronic device 50 on the network.

For each connected electronic device 50, the detection unit 210 is configured to determine whether a monitoring agent 400 is installed or running on the connected electronic device 50. In one embodiment, the detection unit 210 checks whether a monitoring agent 400 is installed or running on a connected electronic device 50 by sending an inquiry to the connected electronic device 50 and waiting for a response to the inquiry. In another embodiment, the device information 220 identifies which of all connected electronic devices 50 already have a monitoring agent 400 installed, and the detection unit 210 checks whether a monitoring agent 400 is already installed on a connected electronic device 50 based on the device information 220.

In response to determining that a monitoring agent 400 is not installed on a connected electronic device 50, the detection unit 210 is configured to trigger installation of the monitoring agent 400 on the connected electronic device 50, and further trigger the monitoring agent 400 to run or start after the installation. In response to determining that a monitoring agent 400 is installed but not running on a connected electronic device 50, the detection unit 210 is configured to trigger the monitoring agent 400 to run or start on the connected electronic device 50. In one embodiment, the detection unit 200 sends a command to a connected electronic device 50 to invoke installation and/or running or starting of a monitoring agent 400 on the electronic device 50.

In one embodiment, installation of a monitoring agent 400 on a connected electronic device 50 comprises the electronic device 50 downloading the monitoring agent 400 from the centralized server device 100, an online digital distribution platform, or another device that maintains and distributes updates for the monitoring agent 400.

In one embodiment, the system 200 maintains user information 230 comprising a profile relating to a particular subset of individual users 30 from all individual users 30 associated with all connected electronic devices 50, wherein each individual user 30 of the subset is hearing impaired. In one embodiment, the system 200 adds an individual user 30 to the subset when the individual user 30 explicitly provides user input, via a connected electronic device 50, indicating that the individual user 30 is hearing impaired. The user input may further indicate a level (i.e., degree) of hearing impairment of the individual user 30 (e.g., permanently hearing impaired or temporarily hearing impaired due to external circumstances or factors). As described in detail later herein, in one embodiment, the system 200 automatically adds an individual user 30 to the subset when the individual user 30 fails to respond to a test pulse output on a connected electronic device 50 associated with the user 30.

In one embodiment, the profile included in the user information 230 indicates, for each individual user 30 of the subset, one or more notification mechanisms suitable for alerting or notifying the individual user 30. In one embodiment, the system 200 adds a particular notification mechanism for an individual user 30 to the profile when the individual user 30 explicitly provides user input, via a connected electronic device 50, indicating that the individual user 30 prefers the particular notification mechanism (e.g., user preferences). As described in detail later herein, in one embodiment, the system 200 automatically selects a particular notification mechanism suitable for an individual user 30, and adds the selected notification mechanism for the individual user 30 to the profile.

In one embodiment, the detection unit 210 is configured to determine a level (e.g., degree) of hearing impairment of an individual user 30 associated with a connected electronic device 50. Examples of different levels of hearing impairment include, but are not limited to, no hearing impairment, temporary hearing impairment due to external circumstances or factors (e.g., a secondary device connected to a connected electronic device 50, an individual user 30 is in a loud or noisy environment), and permanent hearing impairment. In one embodiment, the detection unit 210 is configured to send an audio test pulse to each connected electronic device 50 to assess or determine whether an individual user 30 associated with the electronic device 50 is hearing impaired. In one embodiment, if a connected electronic device 50 is haptic-enabled, the detection unit 210 is configured to send a haptic test pulse to the electronic device 50 to assess or determine whether an individual user 30 associated with the electronic device 50 is hearing impaired.

For example, in one embodiment, the detection unit 210 invokes a monitoring agent 400 on a connected electronic device 50 to produce an audio/haptic test pulse and monitor for a user response to the test pulse from an individual user 30 associated with the electronic device 50. The monitoring agent 400 may detect/capture a user response to the test pulse via an I/O unit 65 or a sensor unit 70 of the electronic device 50. If the monitoring agent 400 does not detect a user response to the test pulse after a pre-determined amount of time (e.g., wait period), the monitoring agent 400 sends a user update data message to the system 200 indicating that the individual user 50 is hearing impaired. If the monitoring agent 400 detects a user response to the test pulse, the monitoring agent 400 sends a user update data message to the system 200 indicating that the individual user 50 is not hearing impaired.

In response to receiving a user update data message from a monitoring agent 400 indicating that an individual user 30 associated with a connected electronic device 50 is hearing impaired, the detection unit 200 is configured to update the profile included in the user information 230 to add the individual user 30. In response to receiving a user update data message from a monitoring agent 400 indicating that an individual user 30 associated with a connected electronic device 50 is not hearing impaired, the detection unit 200 is configured to update the profile included in the user information 230 to remove the individual user 30 (if the individual user 30 is included in the profile).

In one embodiment, a monitoring agent 400 on a connected electronic device 50 is configured to continuously monitor for external circumstances or factors that can affect hearing of an individual user 30 associated with the electronic device 50. In one embodiment, a monitoring agent 400 on a connected electronic device 50 is configured to continuously monitor whether a secondary device is connected to the electronic device 50 via one or more I/O units 65, one or more sensor units 70, or a communications unit 75 of the electronic device 50. For example, the monitoring agent 400 is configured to detect when a secondary device, such as wired headphones or wired loudspeakers, is plugged into a headphone jack or an audio output connector of the electronic device 50. As another example, the monitoring agent 400 is configured to detect when a secondary device, such as wireless headphones or wireless loudspeakers, is wirelessly connected to the electronic device 50 (e.g., via Bluetooth®). In response to detecting a secondary device connected to the electronic device 50, the monitoring agent 400 is configured to send a device update data message to the system 200, wherein the device update data message indicates that the secondary device is connected to the electronic device 50. In one embodiment, the device data update message further comprises contextual information relating to the secondary device and/or an individual user 30 associated with the electronic device 50 (e.g., type of secondary device, whether the secondary device is physically connected or wirelessly connected to the electronic device 50, volume of the secondary device (e.g., headphone volume), location coordinates of the user 30, an IP address of the electronic device 50, etc.)

In one embodiment, a monitoring agent 400 on a connected electronic device 50 is configured to continuously monitor whether an individual user 30 associated with the electronic device 50 is in a loud or noisy environment (e.g., the user 30 is operating loud machinery, the user 30 is at a live event such as a concert or a sports match, etc.) based on ambient noise captured via one or more sensor units 70 of the electronic device 50. In response to detecting the individual user 30 is in a loud or noisy environment, the monitoring agent 400 is configured to send a device update data message to the system 200, wherein the device update data message indicates that the individual user 30 is in a loud or noisy environment. In one embodiment, the device data update message further comprises contextual information relating to the environment and/or an individual user 30 associated with the electronic device 50 (e.g., noise levels in the environment, location coordinates of the user 30, an IP address of the electronic device 50, etc.)

In response to receiving a device update data message from a monitoring agent 400 on a connected electronic device 50, the detection unit 200 is configured to update the profile included in the user information 230 to add an individual user 30 associated with the electronic device 50. Based on the device update date message, the profile may further categorize/classify the individual user 30 as temporarily hearing impaired due to external circumstances or factors (e.g., a secondary device connected to the electronic device 50, the individual user 30 is in a loud or noisy environment). The detection unit 200 is further configured to: (1) determine or select, based on the device data update message and the user information 230, one or more notification mechanisms suitable for alerting or notifying the individual user 30, and (2) update the profile included in the user information 230 to include the one or more notification mechanisms determined or selected for the individual user 30.

For example, if the device update data message indicates that headphones are connected to the electronic device 50 and the user information 230 does not categorize/classify an individual user 30 associated with the electronic device 50 as permanently hearing impaired, the detection unit 200 may determine that producing an audio alert, a haptic alert, and/or a visual alert on the connected electronic device 50 are the notification mechanisms most likely to draw or obtain attention of the individual user 30 (compared to an audio announcement or alert made via a public address system). As another example, if the device update data message indicates that an individual user 30 associated with the electronic device 50 is in a loud or noisy environment and the user information 230 categorizes/classifies the individual user 30 as permanently hearing impaired, the detection unit 200 may determine that producing a haptic alert, a visual alert, and/or a lock alert on the connected electronic device 50 are the notification mechanisms most likely to draw or obtain attention of the individual user 30 (compared to an audio announcement or alert made via a public address system or a speaker of the electronic device 50).

In one embodiment, the system 200 further comprises a notifications unit 240 configured to trigger, for each individual user 30 identified as hearing impaired (based on the user information 230), a monitoring agent 400 on a connected electronic device 50 associated with the individual user 30 to notify the individual user 30 of an event (e.g., an emergency) in accordance with one or more notification mechanisms for the individual user 30 (based on the user information 230).

For example, if the profile included in the user information 230 indicates that an audio notification mechanism is most likely to draw or obtain attention of an individual user 30 who is temporarily hearing impaired due to external circumstances or factors, the notifications unit 240 may invoke a monitoring agent 400 on a connected electronic device 50 associated with the individual user 30 to produce an audio alert. As another example, if the profile included in the user information 230 indicates that a haptic notification mechanism, a visual notification mechanism, and/or a lock notification mechanism are most likely to draw or obtain attention of an individual user 30 identified as permanently hearing impaired, the notifications unit 240 may invoke a monitoring agent 400 on a connected electronic device 50 associated with the individual user 30 to produce a haptic alert, a visual alert, and/or a lock alert.

In one embodiment, the system 200 is configured to build (i.e., train) and update a model 250 based on the device information 220, the user information 230, data messages from monitoring agents 400, and/or user responses from individual users 30 associated with the connected electronic devices 50 (e.g., user responses to alerts, test pulses). In one embodiment, the resulting model 250 is used by the detection unit 210 to categorize/classify an individual user 30 as having no hearing impairment or having some hearing impairment (e.g., temporary hearing impairment due to external circumstances or factors, permanent hearing impairment). For example, in one embodiment, the model 250 is used by the detection unit 210 to determine, for each individual user 30, a corresponding hearing parameter indicative of a level of hearing impairment of the individual user 30. In one embodiment, the detection unit 210 determines or selects a notification mechanism that is best suited for alerting or notifying an individual user 30 based on a corresponding hearing parameter for the individual user 30.

In one embodiment, the system 200 builds and updates the model 250 by applying logistic regression to the device information 220, the user information 230, the data messages, and/or the user responses. In another embodiment, the system 200 builds and updates the model 250 by applying binary classification to the device information 220, the user information 230, the data messages, and/or the user responses. In yet another embodiment, the system 200 builds and updates the model 250 by applying supervised learning to the device information 220, the user information 230, the data messages, and/or the user responses.

Table 1 below provides an example process that the system 200 implements to build a model 250 using logistic regression.

network as the centralized server device 100 on which the system 200 operates. In one embodiment, the system 200 compiles a list of all primary devices 500 (e.g., PRIMARY DEVICE 1, PRIMARY DEVICE 2, . . . , PRIMARY DEVICE n) based on a broadcast of each IP address of each primary device 500 on the network.

Figure 3:
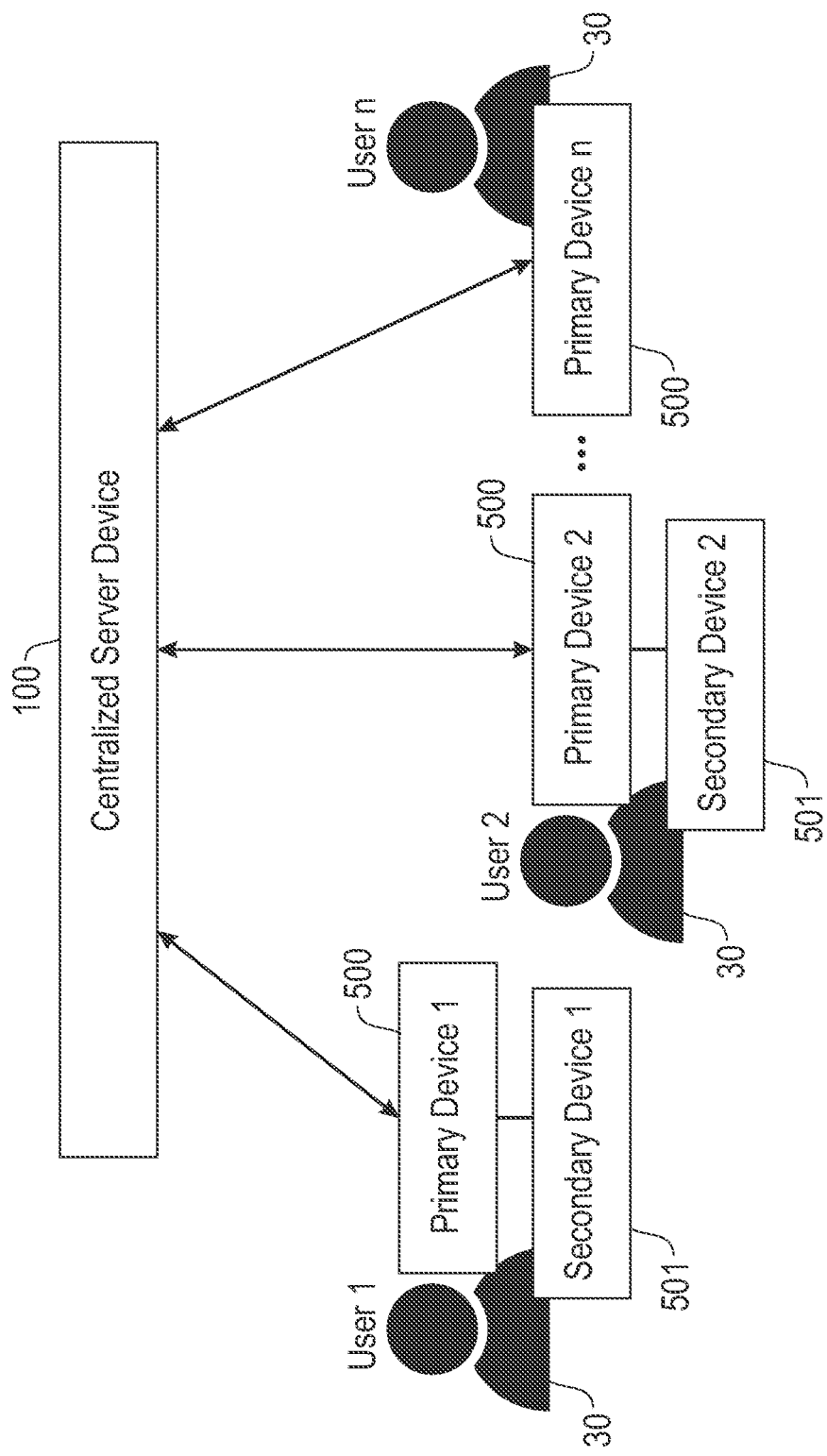
FIG. 3 illustrates an example application scenario utilizing the detection and notification system, in accordance with an embodiment of the invention.

In one embodiment, the system 200 receives a data message from a monitoring agent 400 on a primary device 500, wherein the data message indicates that a secondary device 501 is connected to the primary device 500. For example, as shown in FIG. 3, the system 200 may receive a first data message from a first monitoring agent 400 on PRIMARY DEVICE 1, wherein the first data message indicates that a SECONDARY DEVICE 1 is connected to the PRIMARY DEVICE 1. The system 200 may also receive a second data message from a second monitoring agent 400 on PRIMARY DEVICE 2, wherein the second data message indicates that a SECONDARY DEVICE 2 is connected to the PRIMARY DEVICE 2.

If an event occurs, the system 200 invokes the first monitoring agent 400 on PRIMARY DEVICE 1 and the second monitoring agent 400 on PRIMARY DEVICE 2 to produce an audio/haptic/visual/lock alert that alerts or notifies INDIVIDUAL USER 1 and INDIVIDUAL USER 2, respectively, of the event. If INDIVIDUAL USER n is permanently hearing impaired, the system 200 may invoke

TABLE 1

1. Capture a number of factors using I/O units, sensor units, and/or a communications unit of connected electronic devices. Examples of different factors include, but are not limited to, headphone volume of headphones connected to a connected electronic device, location coordinates (x-coordinate, y-coordinate) of an individual user, etc. Build a table of collected data (i.e., measurements) for the captured factors.

| User ID of individual user | Headphone volume | x-coordinate of individual user's location | y-coordinate of individual user's location | IP Address of Connected Electronic Device | Test Pulse Acknowledged [1 - yes; 0 - no] | Bluetooth ID of Wireless Headphones |
|---|---|---|---|---|---|---|
| 45678abc | 345 | 100 | 100 | 10.5.6.89 | 1 | N/A |
| ert487456 | 126 | 150 | 150 | 10.42.8.7 | 0 | Peter's Cans |
| iut125323 | 2 | 175 | 175 | 10.45.5.61 | 1 | Mary's Headphones |

2. Analyze the collected data using binary regression to obtain a set of model parameters, where lheadvol is a natural log transformation for headphone volume, x_coords is for x-coordinate, and y_coords is for y-coordinate.

| Model Parameter | Estimate | Standard Error | t(*) | t(pr.) | Antilog of Estimate |
|---|---|---|---|---|---|
| Constant | 23.22 | 2.20 | 10.12 | <.001 | 4478578096 |
| lheadvol | −0.45 | 1.05 | −9.94 | <.001 | 0.00002887 |
| x_coords | 0.74 | 0.46 | 0.54 | <.001 | 0.36237263 |
| y_coords | 0.65 | 0.96 | 1.05 | <.001 | 0.67893439 |

3. Using the estimates for the model parameters, obtain a fitted regression line represented as follows:
$\log(p/1 - p) = 23.22 - 0.45 \text{lheadvol} + 0.74 \text{x\_coords} + 0.65 \text{y\_coords}$,
wherein p is a hearing parameter.
4. For each individual user, substitute the model parameters in the fitted regression line with values from a row of the table that corresponds to a User ID of the user to obtain a hearing parameter p for the user
$\log(p/1 - p) = 23.22 - 0.45*345 + 0.74*100 + 0.65*100$
$\log(p/1 - p) = 6.97$
$p/(1 - p) = e^{6.97}$
$p = 1064.222751/(1 + 1064.222751)$
$p = 0.999061033$ FIG. 3 illustrates an example application scenario utilizing the detection and notification system 200, in accordance with an embodiment of the invention. For expository purposes, the term "primary device" as used herein generally refers to an electronic device 50 connected to a same network as the centralized server device 100 on which the a third monitoring agent 400 on PRIMARY DEVICE n to produce a haptic/visual/lock alert that alerts or notifies INDIVIDUAL USER n of the event; otherwise, INDIVIDUAL USER n is alerted or notified of the event via a public address (PA) system instead.

Figure 4:
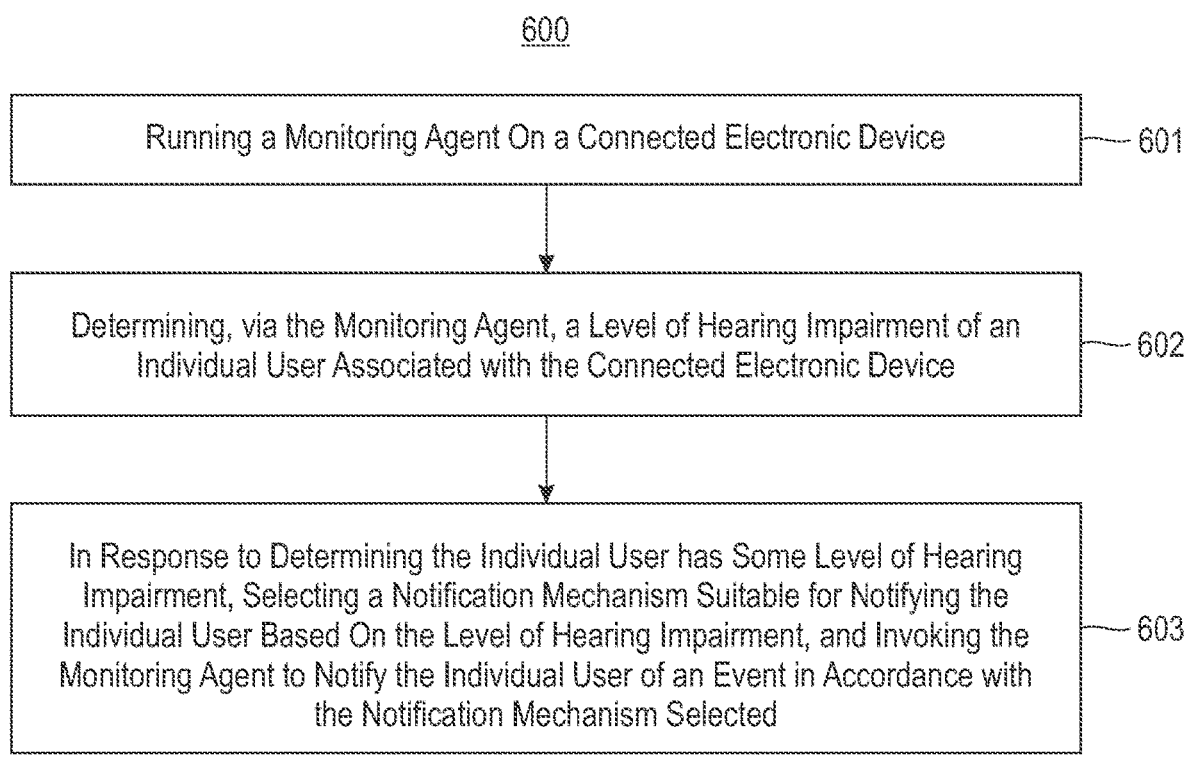
FIG. 4 is a flowchart for an example process for detecting hearing impairment, in accordance with an embodiment of the invention.

FIG. 4 is a flowchart for an example process 600 for detecting hearing impairment, in accordance with an embodiment of the invention. Process block 601 includes running a monitoring agent on a connected electronic device. Process block 602 includes determining, via the monitoring agent, a level of hearing impairment of an individual user associated with the connected electronic device. Process block 603 includes, in response to determining the individual user has some level of hearing impairment, selecting a notification mechanism suitable for notifying the individual user based on the level of hearing impairment, and invoking the monitoring agent to notify the individual user of an event in accordance with the notification mechanism selected.

In one embodiment, process blocks 601-603 are performed by one or more components of the system 200.

Figure 5:
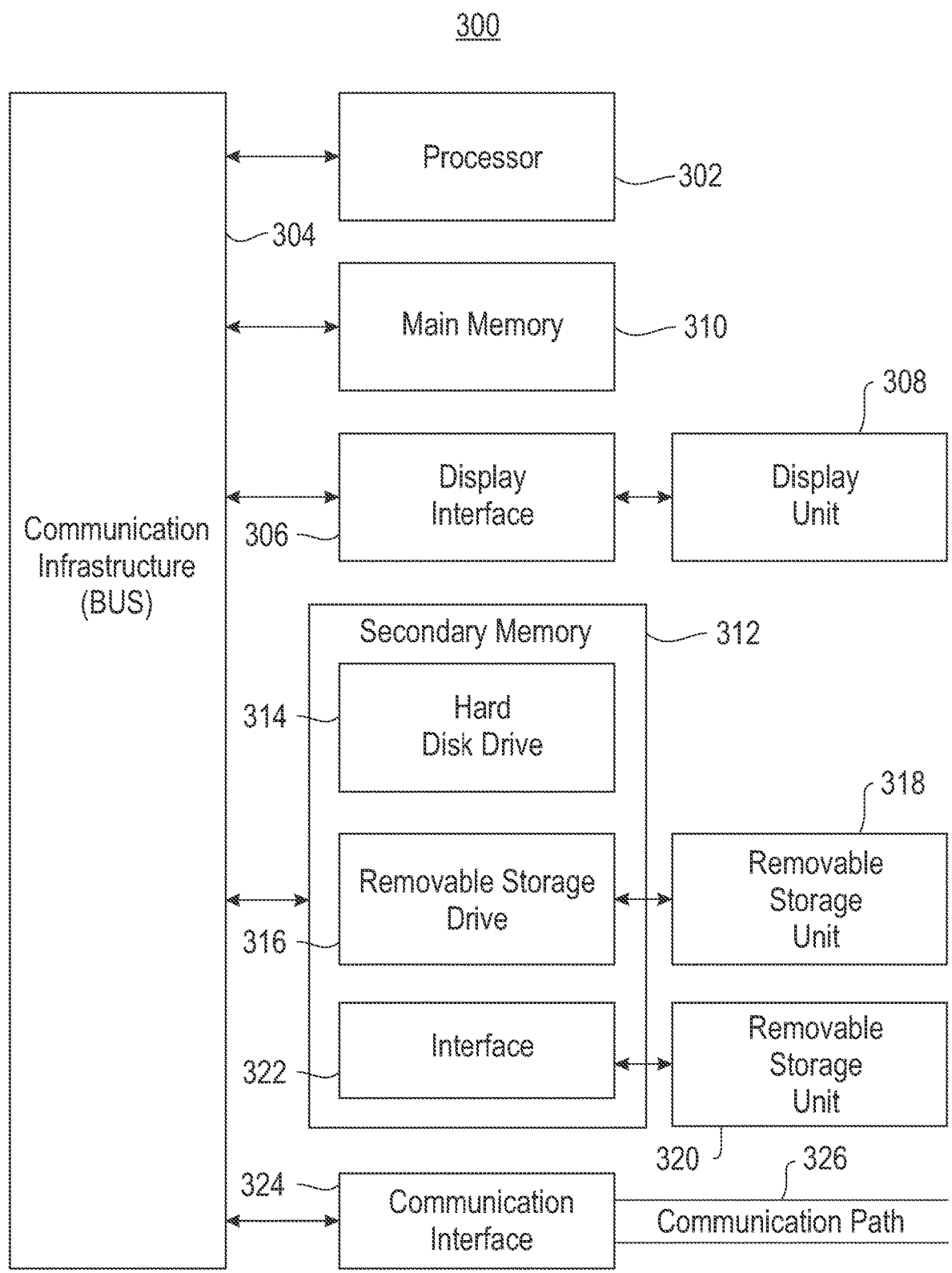
FIG. 5 is a high level block diagram showing an information processing system useful for implementing an embodiment of the present invention.

FIG. 5 is a high level block diagram showing an information processing system 300 useful for implementing one embodiment of the invention. The computer system includes one or more processors, such as processor 302. The processor 302 is connected to a communication infrastructure 304 (e.g., a communications bus, cross-over bar, or network).

The computer system can include a display interface 306 that forwards graphics, text, and other data from the voice communication infrastructure 304 (or from a frame buffer not shown) for display on a display unit 308. In one embodiment, the computer system also includes a main memory 310, preferably random access memory (RAM), and also includes a secondary memory 312. In one embodiment, the secondary memory 312 includes, for example, a hard disk drive 314 and/or a removable storage drive 316, representing, for example, a floppy disk drive, a magnetic tape drive, or an optical disk drive. The removable storage drive 316 reads from and/or writes to a removable storage unit 318 in a manner well known to those having ordinary skill in the art. Removable storage unit 318 represents, for example, a floppy disk, a compact disc, a magnetic tape, or an optical disk, etc. which is read by and written to by removable storage drive 316. As will be appreciated, the removable storage unit 318 includes a computer readable medium having stored therein computer software and/or data.

In alternative embodiments, the secondary memory 312 includes other similar means for allowing computer programs or other instructions to be loaded into the computer system. Such means include, for example, a removable storage unit 320 and an interface 322. Examples of such means include a program package and package interface (such as that found in video game devices), a removable memory chip (such as an EPROM, or PROM) and associated socket, and other removable storage units 320 and interfaces 322, which allows software and data to be transferred from the removable storage unit 320 to the computer system.

In one embodiment, the computer system also includes a communication interface 324. Communication interface 324 allows software and data to be transferred between the computer system and external devices. In one embodiment, examples of communication interface 324 include a modem, a network interface (such as an Ethernet card), a communication port, or a PCMCIA slot and card, etc. In one embodiment, software and data transferred via communication interface 324 are in the form of signals which are, for example, electronic, electromagnetic, optical, or other signals capable of being received by communication interface 324. These signals are provided to communication interface 324 via a communication path (i.e., channel) 326. In one embodiment, this communication path 326 carries signals and is implemented using wire or cable, fiber optics, a phone line, a cellular phone link, an RF link, and/or other communication channels.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

From the above description, it can be seen that embodiments of the present invention provide a system, computer program product, and method for implementing the embodiments of the invention. Embodiments of the present invention further provide a non-transitory computer-useable storage medium for implementing the embodiments of the invention. The non-transitory computer-useable storage medium has a computer-readable program, wherein the program upon being processed on a computer causes the computer to implement the steps of embodiments of the present invention described herein. References in the claims to an element in the singular is not intended to mean "one and only" unless explicitly so stated, but rather "one or more." All structural and functional equivalents to the elements of the above-described exemplary embodiment that are currently known or later come to be known to those of ordinary skill in the art are intended to be encompassed by the present claims. No claim element herein is to be construed under the provisions of 35 U.S.C. section 112, sixth paragraph, unless the element is expressly recited using the phrase "means for" or "step for."

The terminology used herein is for the purpose of describing particular embodiments of the invention only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method comprising: a server device:
running a monitoring agent on an electronic device connected to the server device;
receiving, from the monitoring agent, a data message indicative of a level of hearing impairment of an individual user associated with the electronic device;
classifying the individual user, based in part on the data message, with a classification from a group including permanent hearing impairment, temporary hearing impairment, and no hearing impairment;
selecting a notification mechanism suitable for notifying the individual user based on the classification; and
invoking the monitoring agent to notify the individual user of an event in accordance with the notification mechanism selected.

2. The method of claim 1, further comprising:
the server:
invoking the monitoring agent to produce a test pulse on the electronic device;
waiting for a pre-determined amount of time for a user response from the individual user to the test pulse; and
determining the individual user as having some hearing impairment if no user response is received after the pre-determined amount of time has elapsed.

3. The method of claim 2, wherein the test pulse is an audio test pulse.

4. The method of claim 2, wherein the test pulse is a haptic test pulse.

5. The method of claim 1, further comprising:
the server:
invoking the monitoring agent to continuously monitor whether a secondary device is connected to the electronic device; and
determining the individual user as having some hearing impairment in response to receiving the data message from the monitoring agent indicating that the secondary device is connected to the electronic device.

6. The method of claim 5, wherein the secondary device is one of wired headphones or wired loudspeakers physically connected to the electronic device.

7. The method of claim 5, wherein the secondary device is one of wireless headphones or wireless loudspeakers wirelessly connected to the electronic device.

8. The method of claim 1, further comprising:
the server:
compiling and maintaining a list of all electronic devices connected to the server device based on a broadcast of all IP addresses of the electronic devices.

9. The method of claim 8, further comprising:
the server:
determining which of all individual users associated with the electronic devices have some hearing impairment; and
maintaining a profile indicative of each individual user determined as having some hearing impairment.

10. The method of claim 9, further comprising:
the server:
building and updating a model based on the profile.

11. The method of claim 10, wherein the model results from one of logistic regression, binary classification, or supervised learning.

12. The method of claim 1, wherein the notification mechanism selected comprises at least one of: a haptic notification, an audio notification, a visual notification, or a lock notification.

13. A system comprising:
at least one processor; and
a non-transitory processor-readable memory device storing instructions that when executed by the at least one processor causes the at least one processor to perform operations including:
running a monitoring agent on an electronic device connected to the system;
receiving, from the monitoring agent, a data message indicative of a level of hearing impairment of an individual user associated with the electronic device;
classifying the individual user, based in part on the data message, with a classification from a group including permanent hearing impairment, temporary hearing impairment, and no hearing impairment;
selecting a notification mechanism suitable for notifying the individual user based on the classification; and
invoking the monitoring agent to notify the individual user of an event in accordance with the notification mechanism selected.

14. The system of claim 13, wherein the operations further include:
invoking the monitoring agent to produce a test pulse on the electronic device;
waiting for a pre-determined amount of time for a user response from the individual user to the test pulse; and
determining the individual user as having some hearing impairment if no user response is received after the pre-determined amount of time has elapsed.

15. The system of claim 14, wherein the test pulse is an audio test pulse.

16. The system of claim 14, wherein the test pulse is a haptic test pulse.

17. The system of claim 13, wherein the operations further include:
invoking the monitoring agent to continuously monitor whether a secondary device is connected to the electronic device; and
determining the individual user as having some hearing impairment in response to receiving the data message from the monitoring agent indicating that the secondary device is connected to the electronic device.

18. The system of claim 17, wherein the secondary device is one of wired headphones or wired loudspeakers physically connected to the electronic device.

19. The system of claim 17, wherein the secondary device is one of wireless headphones or wireless loudspeakers wirelessly connected to the electronic device.

20. A non-transitory computer program product comprising a computer readable storage medium having program instructions embodied therewith, the program instructions executable by a processor to cause the processor to:
run a monitoring agent on an electronic device connected to the computer program product;
receive, from the monitoring agent, a data message indicative of a level of hearing impairment of an individual user associated with the electronic device;
classify the individual user, based in part on the data message, with a classification from a group including permanent hearing impairment, temporary hearing impairment, and no hearing impairment;
select a notification mechanism suitable for notifying the individual user based on the classification; and
invoke the monitoring agent to notify the individual user of an event in accordance with the notification mechanism selected.

* * * * *